(12) United States Patent
Tinianov et al.

(10) Patent No.: US 7,254,987 B2
(45) Date of Patent: *Aug. 14, 2007

(54) METHOD AND SYSTEM FOR CONDUCTING AN ON-SITE MEASUREMENT OF THE DENSITY OF AN INSULATION MATERIAL

(75) Inventors: Brandon Dillan Tinianov, Santa Clara, CA (US); Thomas John Fellinger, Littleton, CO (US)

(73) Assignee: Johns Manville, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/032,761

(22) Filed: Jan. 11, 2005

(65) Prior Publication Data

US 2006/0150715 A1   Jul. 13, 2006

(51) Int. Cl.
*G01N 9/24* (2006.01)

(52) U.S. Cl. ......................... 73/32 A; 73/589
(58) Field of Classification Search ................ 73/32 A, 73/589
See application file for complete search history.

(56) References Cited

U.S. PATENT DOCUMENTS 4,672,851 A * 6/1987 Blessing et al. .............. 73/597

6,047,518 A * 4/2000 Lytle ....................... 52/742.13
6,968,740 B2 * 11/2005 Tinianov .................... 73/645

OTHER PUBLICATIONS

ASTM International, Standard Test Method for Impedence and Absorption of Acoustical Materials Using A Tube, Two Microphones and A Digital Frequency Analysis System.
M.E. Delany, E,N. Bazley, Acoustical Properties of Fibrous Absorbent Materials, National Physical Laboratory, Teddington, Middlesex, Gt. Britain.

* cited by examiner

*Primary Examiner*—John E. Chapman
(74) *Attorney, Agent, or Firm*—Robert D. Touslee; Timothy G. Hofmeyer

(57) ABSTRACT

Method for conducting an on-site measurement of a density value of an insulation material is provided, comprising: (a) providing an acoustic source for emitting a sound wave; (b) directing the sound wave emitted from the acoustic source through a waveguide and at an insulation material present in a wall, floor or ceiling cavity; (c) measuring a sound pressure in the waveguide to obtain at least one sound pressure measurement; and (d) calculating a density value of the insulation material based on the at least one sound pressure measurement.

22 Claims, 1 Drawing Sheet

METHOD AND SYSTEM FOR CONDUCTING AN ON-SITE MEASUREMENT OF THE DENSITY OF AN INSULATION MATERIAL

BACKGROUND

It can be desirable to determine a characteristic of an insulation material such as, for example, a thermal and/or sound insulation material for use in a residential and/or commercial building. For example, to determine whether an insulation material is suitable for use in a specific application, it can be desirable to determine the density of such material.

A thermal and/or sound insulation product can be formed by blowing insulation material such as fiberglass and an adhesive onto a surface, and curing the blown-in materials. This method can be used in the formation of, for example, insulation product between wall studs, ceiling joists, floor joists or combinations thereof. Installing such "blown-in" insulation product can be more convenient and/or cost-effective in comparison with installing conventional preformed insulation material. Methods and systems for forming such blown-in insulation product are discussed in, for example, U.S. Pat. Nos. 4,712,347, 5,287,674 and 5,641,368.

Characteristics of such "blown-in" insulation product such as the density thereof can be altered by varying parameters of the blowing process. For example, the density of the cured product can be affected by the ratio of the amount of fiberglass used to the amount of adhesive used, the particular equipment used to apply the blown-in material, and/or the manner in which the materials are applied. Thus, it can be desirable to determine whether such blown-in product meets certain density specifications.

Generally, various known methods exist for measuring the density of an insulation material. Some known methods require the removal of a sample of the insulation material from its installed, preferred location and/or the destruction of such sample in order to determine the density thereof. However, the removal and/or destruction of a sample in order to measure the density of an insulation material can be inconvenient, inefficient and/or time consuming.

In view of the above, it is apparent that it can be desirable to enable measurement of the density of an insulation material by non-destructive means, and/or without the need for removing such insulation material from its preferred, installed location.

SUMMARY

According to one aspect, a method for conducting an on-site measurement of a density value of an insulation material is provided, comprising:

(a) providing an acoustic source for emitting a sound wave;

(b) directing the sound wave emitted from the acoustic source through a waveguide and at an insulation material present in a wall, floor or ceiling cavity;

(c) measuring a sound pressure in the waveguide to obtain at least one sound pressure measurement; and (d) calculating a density value of the insulation material based on the at least one sound pressure measurement.

According to another aspect, a system for conducting an on-site measurement of a density value of an insulation material is provided, comprising an acoustic source for emitting a sound wave, a waveguide for directing the sound wave at an insulation material present in a wall, floor or ceiling cavity, and at least one sound pressure sensor arranged to measure a sound pressure in the waveguide.

DETAILED DESCRIPTION

Figure 1:
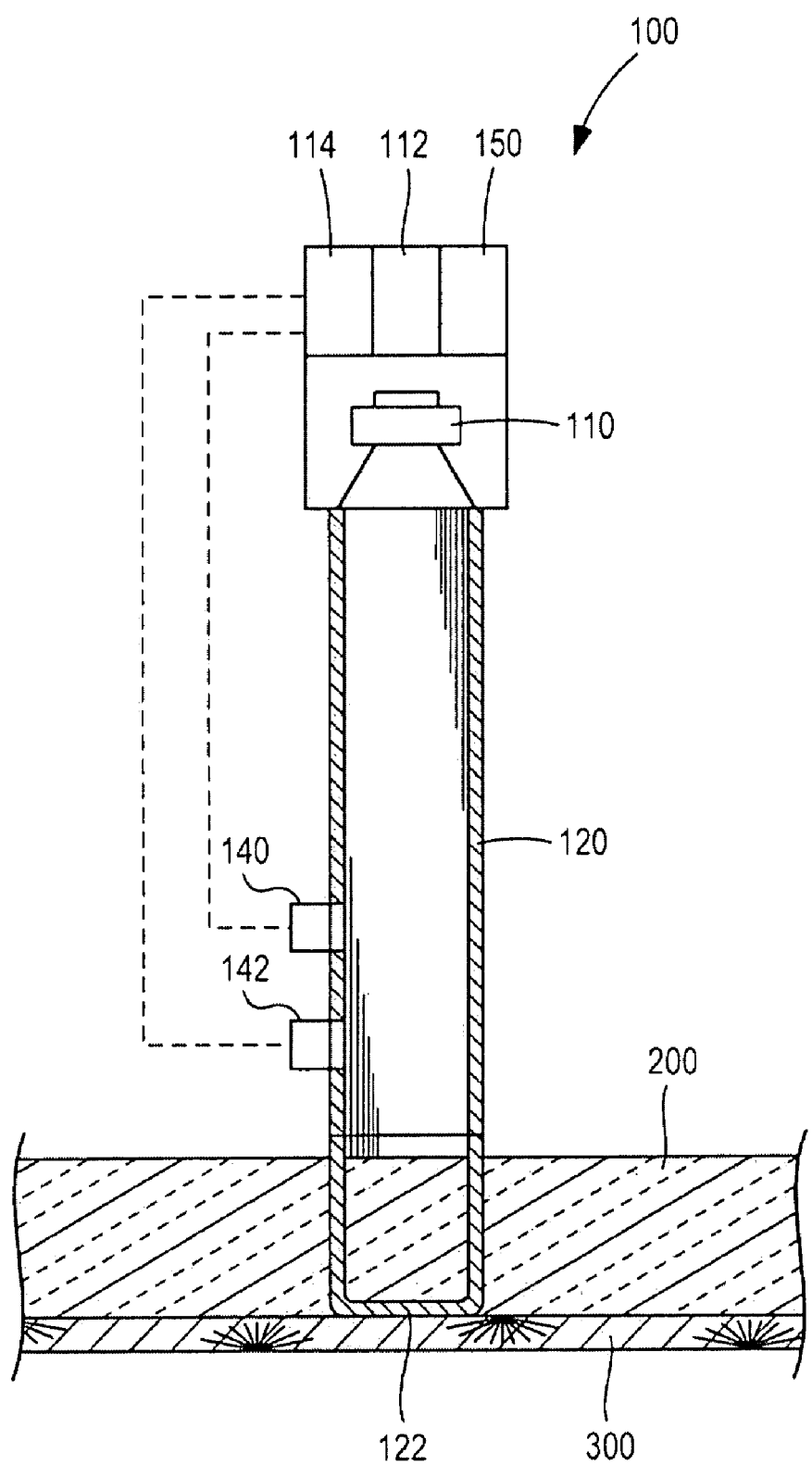
FIG. 1 is a cross-sectional side view of an exemplary system for the on-site measurement of the density of an insulation material.

Methods and systems suitable for the on-site measurement of a density value of an insulation material are provided. For example, an exemplary method can reduce or avoid the need for removing a sample for offsite testing. An exemplary system can include use of a portable device which enables convenient transport to and from the site at which the insulation material is located.

Exemplary embodiments can enable the on-site measurement of a density value of the insulation material, for example, at a residential or commercial building in which the insulation material is installed. For example, the insulation material can be present in a wall, floor or ceiling cavity. The wall, floor or ceiling cavity can be at least partially defined by a rigid acoustic reflecting material which can be made of any suitable material such as, for example, wood, gypsum board, oriented strand board, sheathing or a combination thereof. Preferably, the rigid acoustic reflecting material can at least partially constitute the back surface of the wall, floor or ceiling cavity. In addition, the wall, floor or ceiling cavity can be at least partially defined by at least two wall studs, floor joists or ceiling joists. In a preferred embodiment, the wall, floor or ceiling cavity can be at least partially defined by adjacent, substantially parallel wall studs and a rigid acoustic reflecting material. For example, an exemplary wall cavity can be formed by vertically oriented, commercially available two-by-four inch wooden beams, 8 feet high and 16 inches on center, and a rigid acoustic reflecting material.

Preferably, an exemplary embodiment can provide a non-destructive means for measuring a density value of the insulation material. An exemplary embodiment can also enable measurement of a density value of the insulation material without requiring the removal of a sample of such material from a preferred, installed location. In an exemplary embodiment, the density value of such material can be measured substantially without removal of a portion of the insulation material from the wall, floor or ceiling cavity. For example, the density value can be measured without removal of an amount of insulation material useful for off-site testing of such material. By providing an on-site, non-destructive means for measuring a density value of the insulation material according to one aspect, the time and effort associated with obtaining a sample of the insulation material and conducting off-site tests thereof can be reduced or avoided.

The method for measuring a density value of an insulation material can include providing an acoustic source for emitting a sound wave. For example, the acoustic source can be any device suitable for emitting a sound wave that is detectable by conventional means and can include, for example, a speaker. In an exemplary embodiment, the acoustic source can include a 50 mm high-performance compression driver. A compression driver which can be used is available from Peavey Electronics Corporation, located in Meridian, Miss., as well as B&C Speakers SPA, located in Italy. The acoustic source can emit sound waves continuously or intermittently.

The frequency of the sound wave emitted from the acoustic source can be selected, for example, depending on the particular insulation material to be tested. For example, the frequency employed for an insulation material primarily formed from glass fibers and a binder material can be from about 500 to about 2,000 Hz, more preferably about 1000 Hz.

A signal generator and an amplifier can be used for providing a signal to the acoustic source, and amplifying the signal provided to the acoustic source, respectively. Any signal generator capable of generating a signal for use with the acoustic source can be employed. For example, the frequency of the sound wave emitted by the acoustic source can be controlled by the signal generator. In an exemplary embodiment, an analog output card for use with a computer can be used such as a static analog voltage output card, Model No. PCI-6703, available from National Instruments Corporation located in Austin, Tex. Exemplary amplifiers which can be used are available from AudioSource, Inc., located in Portland, Oreg.; Peavey Electronics Corporation, located in Meridian, Miss.; and Crown Audio, Inc., located in Elkhart, Ind.

The sound wave emitted from the acoustic source can be directed through a waveguide and at an insulation material. The waveguide can have any structure, for example, that is suitable for directing the sound wave emitted from the acoustic source to a particular area of the insulation material. In an exemplary embodiment, the waveguide can provide a well-controlled sound field to improve the accuracy of the measurement of the density of the insulation material and/or to at least partially isolate the space inside the waveguide from outside noise which may adversely affect the accuracy of measurements being taken. Preferably, one end of the waveguide can be connected to the acoustic source to enable the acoustic source to direct the sound wave in the direction of the length of the waveguide. The opposite end of the waveguide can terminate proximate to or in contact with the insulation material. In an exemplary embodiment, the two ends of the waveguide can be the only openings in the waveguide.

The waveguide can have any structure suitable for accommodating the passage of the sound wave therethrough. Preferably, the waveguide can have structure suitable for obtaining accurate sound pressure measurements. Preferably, the waveguide can have an elongated, hollow structure defining a lengthwise passage through which the sound wave can travel. For example, the waveguide can have a circular or elliptical cross-sectional profile. Alternatively, the waveguide can have a rectangular or square-shaped cross-sectional profile. The waveguide can have a smooth, nonporous interior surface to reduce or avoid inaccuracies of the sound pressure measurements caused by the interior surfaces.

The waveguide can have any dimensions suitable for accommodating the passage of the sound wave therethrough. Preferably, the waveguide can have dimensions suitable for obtaining accurate sound pressure measurements. For example, the inside diameter of the waveguide can be from about 12 to about 100 mm, more preferably from about 20 to about 70 mm. The length of the waveguide can depend on at least the inside diameter of the waveguide and/or the position of sound pressure sensors arranged therein, and preferably can be at least about twelve times the diameter of the waveguide. For example, the length of the waveguide can be from about 144 mm to about 2 meters, more preferably from about 200 to about 400 mm. The waveguide can be sufficiently thick to reduce or substantially eliminate sound transmission through the wall of the waveguide.

In an exemplary embodiment, the waveguide can possess dimensions which are effective to establish a plane wave acoustic field directed at the insulation material. Establishing a plane wave acoustic field can, for example, enable the calculation of density measurements using two sound pressure sensors.

The waveguide can be formed from any rigid material suitable for accommodating the passage of a sound wave therethrough such as a plastic, a metal or an alloy. Preferably, the waveguide can be formed from aluminum or an aluminum alloy.

The insulation material subject to density measurement can include any insulation material which has a density that is measurable by the present methods and systems. For example, the insulation material can include a thermal and/or sound insulation material. Preferably, the insulation material can be formed from at least fiberglass and a binder material. In an exemplary embodiment, the insulation material can include a "blown-in" thermal and/or sound insulation material which is formed by blowing a fiberglass insulation material and an adhesive at a surface to be insulated. Methods and systems for forming such an insulation product are discussed in, for example, U.S. Pat. Nos. 4,712,347, 5,287,674 and 5,641,368, the contents of which are herein incorporated by reference.

The insulation material can be a wet-applied material and have a relatively high moisture content prior to being fully cured. An example of a wet-applied material is the blown-in insulation material described above. It can be useful to determine the density of the insulation material prior to curing, during curing and/or after the insulation material is fully cured. Accordingly, the systems and methods can be used prior to, during and/or after complete curing of such wet-applied material. Preferably, the present devices and systems can at least be used after complete curing.

The insulation material can have any shape which enables the measurement of the density thereof using the present systems and methods. For example, in the case of a blown-in insulation material, the insulation material can at least partially take the form of the cavity into which the material is blown. The insulation can have dimensions that enable measurement of the density of the insulation by the system and method described herein. For example, the thickness of the insulation material, i.e., the depth of the insulation material in the cavity, can be about 4 inches or less.

The insulation material can be substantially homogeneous, in which case the density measurement of a portion of the insulation material can be substantially representative of the insulation material as a whole. However, the insulation material is not limited to being substantially homogeneous, and the degree of homogeneity can depend on the manner in which the insulation material is produced. The degree of homogeneity of the blown-in insulation material can depend on several factors including, for example, the composition of the insulation material and/or the manner in which the uncured insulation material is applied. In a case where the density of the insulation material is not substantially homogeneous, the methods and systems can be used to measure the density of various parts of the insulation material.

The sound pressure can be measured at least at one location between the acoustic source and the insulation material, preferably inside the waveguide. In an exemplary embodiment, sound pressures can be measured at least at two locations between the acoustic source and the insulation material, preferably inside the waveguide. When sound pressures are taken at multiple locations, the measurements can be taken at different times and/or simultaneously.

The sound pressure measurements can be conducted, for example, while the acoustic source is directing a sound wave into the waveguide. The sound pressure measurements can be taken on an intermittent or continuous basis. To enable accurate sound pressure measurement, an acoustic reflecting material such as a surface of the wall, floor or ceiling cavity can be arranged to face the acoustic source and to reflect acoustic energy.

At least one sound pressure sensor can be provided for conducting sound pressure level measurements, for example, during emission of a sound wave from the acoustic source. In one embodiment, a single sound pressure sensor can be used to measure the sound pressure, for example, in a timed gate. For example, the sound pressure sensor can initially measure the incident sound pressure level, and then the reflected sound. The at least one sound pressure sensor can measure sound pressure on a continuous or intermittent basis.

The at least one sound pressure sensor can be located, for example, from about 50 to about 750 mm, more preferably from about 100 to about 200 mm, from the acoustic source. The at least one sound pressure sensor can also be located, for example, from about 50 to about 750 mm, more preferably from about 100 to about 200 mm, from the end of the waveguide proximate to the insulation material.

In an exemplary embodiment, at least two sound pressure sensors can be used which are arranged a distance apart from each other. The use of at least two sound pressure sensors can be effective to obtain two sound pressure measurements inside the waveguide, and to enable the determination of a sound pressure differential between the two sound pressure sensors. Preferably, the at least two sound pressure sensors can be arranged at or within the sidewall of the waveguide, for example, flush or recessed with respect to the interior surface of the waveguide.

The at least two first and second sound pressure sensors can be arranged by being spaced a distance apart from each other, for example, from about 10 to about 50 mm apart, more preferably from about 10 to about 25 mm apart. Each of the sound pressure sensors can be located a predetermined distance from the acoustic source, for example, from about 50 to about 750 mm, more preferably from about 100 to about 200 mm. Each of the sound pressure sensors can also be located a predetermined distance from the end of the waveguide proximate to the insulation material, for example, from about 50 to about 750 mm, more preferably from about 100 to about 200 mm.

Any device suitable for measuring sound pressure can be used as the sound pressure sensor(s) discussed above. For example, a microphone can be used such as a ¼-inch ICP pressure microphone available from G.R.A.S. Sound and Vibration, located in Vedbaek, Denmark. The sound pressure sensor(s) can be used with additional devices to enable the device to operate properly in, for example, a noisy environment. In an exemplary embodiment, a phase-sensitive rectifier, a low pass filter and/or a lock-in amplifier can be used to improve signal-to-noise ratios. Such devices can be driven by software available from National Instruments Corp. located in Austin, Tex., under the trade name LabVIEW.

In one embodiment, the sound pressure sensor(s) can provide analog signals which can be converted to digital signals to facilitate signal processing. Any suitable means for acquiring the digital signals can be used including, for example, a computer used with a dynamic signal acquisition board, Model PCI-4452, available from National Instruments Corp. Alternatively, the signals can be processed in analog format.

A density value of the insulation material can be calculated based on the sound pressure measurements. Techniques for estimating the density based on acoustic measurements are discussed in, for example, ASTM E 1050-98, "Standard Test Method for Impedance and Absorption of Acoustical Materials using a Tube, Two Microphones and a Digital Frequency Analysis System", American Society for Testing and Materials, and M. E. Delany at al., "Acoustical Properties of Fibrous Absorbent Materials", Applied Acoustics, 3, pg. 105-116 (1970). the contents of which are incorporated herein by reference. For example, as discussed in ASTM E 1050-98, the test method can be applied to measure sound absorption coefficients of absorptive materials at normal incidence, and it also can be used to determine specific impedance and admittance ratios. Delany et al. for example, discusses the relationship between the bulk density of a material and other properties of such material.

Any apparatus suitable for calculating a density value of the insulation material based on the sound pressure measurements can be used. For example, an analyzer can be used which is arranged to receive the sound pressure measurements from the at least one sound pressure sensor. The at least one sound pressure sensor can provide measurements to the analyzer on a continuous basis or an intermittent basis. In a preferred embodiment, the analyzer, acoustic source and waveguide can be connected together to form a portable handheld device. Alternatively, the analyzer can be a separate unit from the waveguide and acoustic source assembly.

The analyzer can be capable of receiving sound pressure measurements from the at least one sensor, and processing such data to calculate the density of the insulation material. For example, the analyzer can include any suitable means for receiving and processing data such as computer hardware and/or software. For example, the sound pressure measurements can be inputted into a formula or algorithm to obtain an estimate of the density of the insulation material.

Referring to FIG. 1, an exemplary device 100 for measuring the density of the insulation material 200 can include an acoustic source 110 such as a speaker arranged to direct a sound wave at the insulation material 200. The device 100 can also include a signal generator 112 and an amplifier 114 for providing a signal and amplifying the signal provided to the acoustic source 110. The device 100 can include a waveguide 120 arranged between the acoustic source 110 and the insulation material 200. The waveguide 120 can have a flange 130 disposed at an end thereof.

At least one sound pressure sensor can be provided for conducting sound pressure level measurements at a location between the acoustic source 116 and the insulation material 200. FIG. 1 shows an embodiment employing first and second sound pressure sensors 140 and 142. Such sensors can be positioned a distance apart from each other to obtain first and second sound pressure measurements inside the waveguide 120, respectively. Preferably, the first and second sound pressure sensors 140 and 142 can be arranged at the sidewall of the waveguide 120, for example, flush or recessed with respect to the interior surface of the waveguide 120.

The device 100 can include an analyzer 150 which is arranged to receive the sound pressure measurements from the sound pressure sensor(s). The analyzer 150 can be capable of receiving sound pressure measurements from the sensor(s), and processing such data to estimate the density of the insulation material 200.

In an exemplary embodiment, a waveguide cap 122 can be provided which is capable of attachment to an end of the waveguide 120. The waveguide cap 122 can have any structure capable of containing insulation material, and is open at one end to allow sound waves to be directed to such insulation material. For example, use of the waveguide cap 122 in conjunction with the corresponding end of the waveguide 120 can improve the accuracy of sound pressure measurements conducted by the at least one sound pressure sensor. Any suitable means for attaching the end of the waveguide 120 to the waveguide cap 122 can be used. For example, the corresponding ends of the waveguide 120 and the waveguide cap 122 can form a pressure-fit or threaded engagement. Preferably, the waveguide cap 122 and the end of the waveguide 120 can form a substantially air-tight seal when attached together.

Preferably, the waveguide cap 122 can be used in an embodiment wherein the insulation material 200 is formed by the blown-in method described above. The waveguide cap 122 can contain a portion of the insulation material 200. For example, the waveguide cap 122 can be attached to the rigid acoustic reflecting material 300 prior to blowing the uncured product, and the waveguide cap 122 can be at least partially filled with the uncured product during blowing. The waveguide cap 122 can be fastened to the rigid acoustic reflecting material 300 by any suitable means such as by use of an adhesive and/or mechanical means such as by stapling the waveguide cap 122 to the rigid acoustic reflecting material 300. After blowing and curing, the waveguide cap 122 can be at least partially filled with the insulation material 200, and the waveguide cap 122 can be at least partially embedded in the insulation material 200.

The waveguide cap 122 can be formed from any suitable material such as a plastic, metal or alloy. Preferably, the waveguide cap 122 can be formed from aluminum or an aluminum alloy.

While the invention has been described with reference to exemplary embodiments, it is understood that variations and modifications may be resorted to as will be apparent to those skilled in the art. Such variations and modifications are to be considered within the scope of the invention as defined by the claims appended hereto.

What is claimed is:

1. A method for conducting an on-site measurement of a density value of an insulation material, comprising:
    (a) providing an acoustic source for emitting a sound wave;
    (b) directing the sound wave emitted from the acoustic source through a waveguide and at an insulation material present in a wall, floor or ceiling cavity;
    (c) measuring a sound pressure in the waveguide to obtain at least one sound pressure measurement; and
    (d) calculating a density value of the insulation material based on the at least one sound pressure measurement.

2. The method according to claim 1, wherein a surface of the wall, floor or ceiling cavity that faces the acoustic source is at least partially formed from a rigid acoustic reflecting material.

3. The method according to claim 2, wherein the rigid acoustic reflecting material comprises wood, gypsum board, oriented strand board, sheathing or a combination thereof.

4. The method according to claim 2, wherein the wall, floor or ceiling cavity is at least partially defined by a rigid acoustic reflecting material and at least two wall studs, floor joists or ceiling joists.

5. The method according to claim 1, wherein the acoustic source is attached to an end of the waveguide.

6. The method according to claim 1, wherein the acoustic source is a speaker.

7. The method according to claim 1, wherein the step of measuring the sound pressure in the waveguide is conducted with at least one sound pressure sensor arranged on or within an inner wall of the waveguide.

8. The method according to claim 1, further comprising:
    arranging a waveguide cap in the wall, floor or ceiling cavity such that the waveguide cap is at least partially filled with a portion of the insulation material after the insulation material is applied to the wall, floor or ceiling cavity.

9. The method according to claim 8, wherein after the insulation material is applied to the wall, floor or ceiling cavity, the waveguide cap is at least partially embedded in the insulation material.

10. The method according to claim 8, further comprising attaching the waveguide cap to the waveguide.

11. The method according to claim 1, wherein the density value of the insulation material is calculated substantially without removal of an amount of the insulation material from the wall, floor or ceiling cavity.

12. A system for conducting an on-site measurement of a density value of an insulation material, comprising:
    an insulation material present in a wall, floor or ceiling cavity, and
    an acoustic source for emitting a sound wave, a waveguide for directing the sound wave at the insulation material present in a wall, floor or ceiling cavity, and at least one sound pressure sensor arranged to measure a sound pressure in the waveguide.

13. The system according to claim 12, wherein the acoustic source is attached to an end of the waveguide.

14. The system according to claim 12, wherein the acoustic source is a speaker.

15. The system according to claim 12, wherein the waveguide comprises an elongated, hollow structure.

16. The system according to claim 12, wherein the at least one sound pressure sensor is arranged on or within an inner wall of the waveguide.

17. A system comprising:
    an insulation material present in a wall, floor or ceiling cavity,
    an acoustic source for emitting a sound wave,
    a waveguide for directing the sound wave at the insulation material present in the wall, floor or ceiling cavity, and
    at least one sound pressure sensor arranged to measure a sound pressure in the waveguide,
    wherein a surface of the wall, floor or ceiling cavity that faces the acoustic source is at least partially formed from a rigid acoustic reflecting material.

18. The system according to claim 17, wherein the rigid acoustic reflecting material comprises wood, gypsum board, oriented strand board, sheathing or a combination thereof.

19. The system according to claim 17, wherein the wall, floor or ceiling cavity is at least partially defined by a rigid acoustic reflecting material and at least two wall studs, floor joists or ceiling joists.

20. The system according to claim 17, further comprising a waveguide cap for attachment to the waveguide, wherein the waveguide cap is at least partially filled with a portion of the insulation material, wherein the waveguide cap is at least partially embedded in the insulation material.

21. A system for conducting an on-site measurement of a density value of an insulation material, comprising:

an acoustic source for emitting a Sound wave, a waveguide far directing the sound wave at an insulation material present in a wall, floor or ceiling cavity, and at least one sound pressure sensor arranged to measure a sound pressure in the waveguide, and a waveguide cap for attachment to the waveguide, wherein the waveguide cap is at least partially filled with a portion of the insulation material.

22. The system according to claim 21, wherein the waveguide cap and an end of the waveguide are capable of forming a pressure-fit or threaded engagement.

* * * * *